United States Patent [19]

Boute et al.

[11] Patent Number: 4,503,857
[45] Date of Patent: Mar. 12, 1985

[54] PROGRAMMABLE CARDIAC PACEMAKER WITH MICROPROCESSOR CONTROL OF PACER RATE

[75] Inventors: Willem Boute, Doesburg; Frederik H. M. Wittkampf, Brummen; Gerrit W. van Arragon, Dieren; Kornelis A. Mensink, Brummen, all of Netherlands

[73] Assignee: Vitatron Medical B.V., Netherlands

[21] Appl. No.: 436,411

[22] Filed: Oct. 25, 1982

[30] Foreign Application Priority Data

Oct. 26, 1981 [EP] European Pat. Off. ........ 81108940.8

[51] Int. Cl.³ .............................................. A61N 1/36
[52] U.S. Cl. ............................................. 128/419 PG
[58] Field of Search ................................. 128/419 PG

[56] References Cited
U.S. PATENT DOCUMENTS

| 3,693,626 | 9/1972 | Cole | 128/419 P |
| 3,747,604 | 7/1973 | Berkovits | 128/419 PG |
| 3,794,045 | 2/1974 | Thaler | 128/419 P |
| 3,807,410 | 4/1974 | Wall et al. | 128/419 PG |
| 3,857,399 | 12/1974 | Zacouto | 128/419 PG |
| 3,903,897 | 9/1975 | Woollons et al. | 128/419 PG |
| 3,921,642 | 11/1975 | Preston et al. | 128/419 PG |
| 4,163,451 | 8/1979 | Lesnick et al. | 128/419 PG |
| 4,169,480 | 10/1979 | Digby et al. | 128/419 PG |
| 4,228,803 | 10/1980 | Rickards | 128/419 PG |
| 4,298,007 | 11/1981 | Wright et al. | 128/419 PG |
| 4,313,441 | 2/1982 | Buffet | 128/419 PG |
| 4,428,378 | 11/1984 | Anderson et al. | 128/419 PG |

Primary Examiner—William E. Kamm
Attorney, Agent, or Firm—Woodcock Washburn Kurtz Mackiewicz & Norris

[57] ABSTRACT

A programmable pacemaker apparatus having a microprocessor and means for receiving program information from an external source, means for generating and delivering stimulus signals and means for sensing the occurrence of natural heartbeats in a patient, and having a battery source powering the apparatus, said microprocessor being combined with program instructions stored in memory for controlling the operation of said pacemaker, comprising controller circuit means external to said microprocessor and interconnected therewith for controlling the operating state of said microprocessor, said controller means having occurrence means for determining the occurrence of given events. The controller means further comprises means for stopping operation of the microprocessor on command from the microprocessor and for starting operation of the microprocessor upon determination of one of said events, whereby the microprocessor normally is on less than about 25% of the time. The pacemaker provides for at least two modes of pacing rate control, whereby the patient's heartbeat can be overdriven, or abrupt changes in rate are not followed beyond a selected rate change limit. Means are provided for microprocessor control of testing of pacemaker conditions, and for limiting current to the pacemaker output circuit when the battery voltage drops below a predetermined value.

17 Claims, 14 Drawing Figures

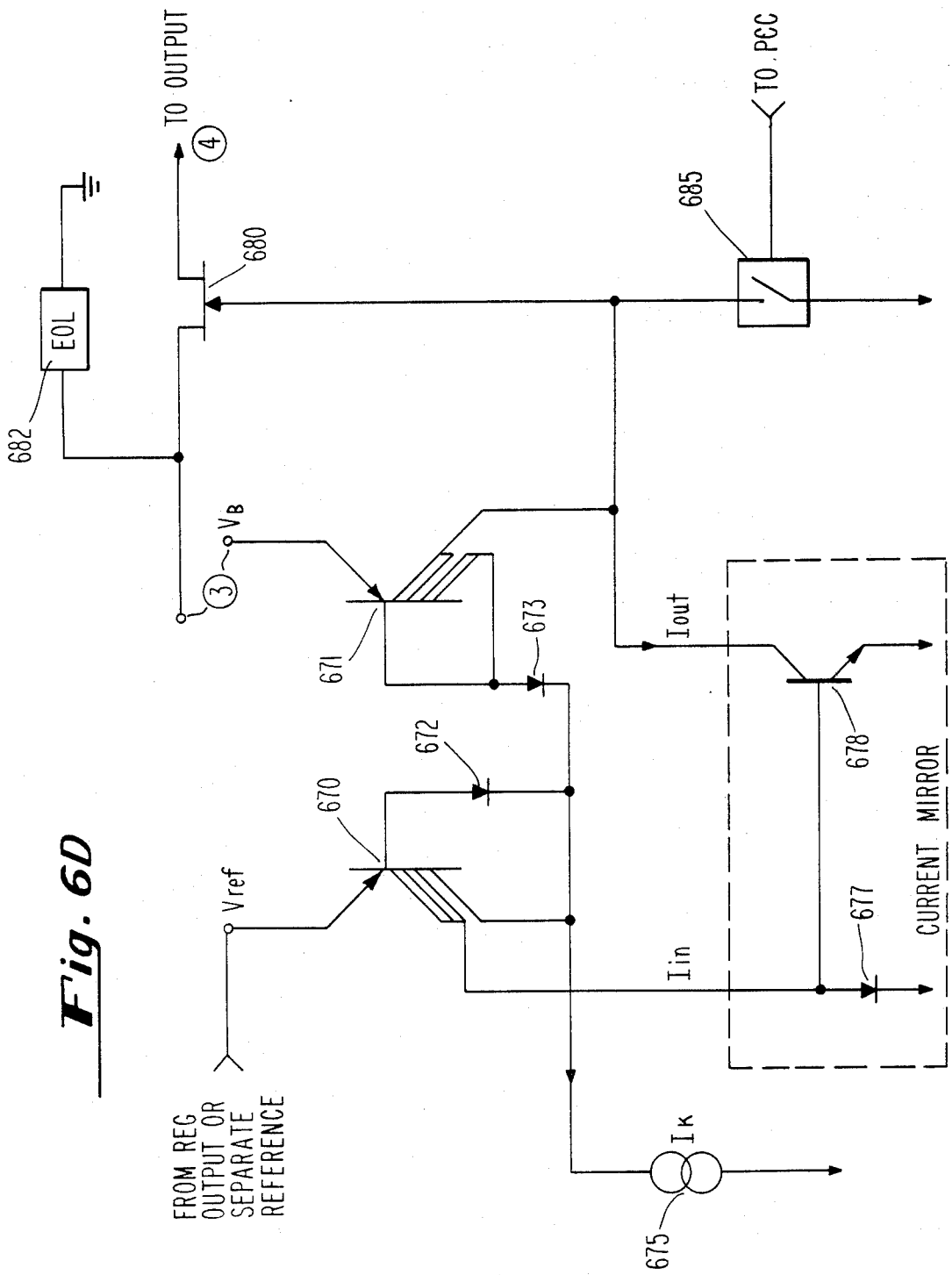

PROGRAMMABLE CARDIAC PACEMAKER WITH MICROPROCESSOR CONTROL OF PACER RATE

BACKGROUND OF THE INVENTION

This invention relates to a programmable cardiac pacer and, in particular, a pacer with means and a method to vary the pacing rate in response to sensed heartbeat signals in a manner dependent upon one of a plurality of programmed modes and the timing of the sensed heartbeat compared to the prior pacer cycle or cycles.

Pacemaker design has evolved very rapidly over the last several years. There has been a great deal of work in enhancing the programmability of pacemakers, to enable them to be programmed to work with different selected operating parameters, and indeed to work in different modes. The evolution of pacemaker design has further led to the incorporation of a microprocessor into the pacemaker apparatus as a central means for providing flexible programming and control of the pacemaker operation. Incorporation of a microprocessor into cardiac pacers has been made possible by the development of a relatively low power microprocessor CPU as, for example, the CDP 1802. The CDP 1802 utilizes CMOS technology, and operates at a relatively low power with a voltage supply conveniently provided by an available lithium battery. For multiprogrammable pacemaker applications such a microprocessor is well suited for carrying out desired subroutines, interrupts and accessing program data, and provides good capability for software control of the pacer operation. Such a microprocessor is thus a highly suitable element in an overall design for a pacemaker which enables programming of multiple parameters of the pacer operation. Further, the speed and increased flexibility of microprocessor control enables cycle to cycle adjustments, permitting the pacer design to optimize one or more selected parameters, such as pacer rate and escape interval, in view of sensed cardiac conditions.

Control of pacing rate and escape interval are very important in a pacemaker system, for a variety of reasons. As used in this specification, the term pacing interval is the time interval between two consecutive delivered pacing pulses, while the term escape interval means the time that the pacemaker waits from a last sensed heartbeat until generation of a next pacing pulse. For a demand pacer, if a natural pulse occurs before the escape interval has timed out, the cycle is re-initiated, and timing of the escape interval starts over again. As used herein, the terms pacer cycle or cycle refer to the interval between a natural or paced heartbeat and the next natural heartbeat or delivered pacing signal.

In conventional demand pacers with hysteresis, the escape interval is greater than the pacing interval, thereby enabling the patient's natural pacemaker to continue to control the heart as long as the rate is maintained above a predetermined minimum.

Prior art pacemakers have recognized problems that can occur in the event of natural heartbeats at rates substantially above the normal programmed rate. In particular, such problems are acute when these changes are abrupt, e.g., when natural heartbeats suddenly occur at a rate far above the pacing rate. It is important that a pacemaker have means to stabilize irregular natural rhythms, such as occur with sick sinus syndrome. It is desirable to allow spontaneous activity to the extent possible, but it is likewise desirable to control such activity within safe limits. For example, the prior art shows the technique of keeping track of a spontaneous or natural heartbeat rate, but without intervening unless such rate goes above a predetermined maximum. While such tracking permits pacer capture at a rate corresponding to the last spontaneous rate when the spontaneous beats disappear, there is no limitation on the abruptness with which the spontaneous heartbeats are permitted to occur. On the contrary, it is frequently desirable to reduce the effect of premature ventricular contractions or random ectopics, and to continue pacing with relatively slower controlled changes in rate. Further, it is our observation that it is often preferrable not to adapt the pacing rate automatically to overcome or overdrive all heart irregularities, but rather to allow changes at any rate between prescribed minimum and maximum values so long as the rate of change is within allowable limits.

Another area of pacemaker rate control that is very important is that of adapting to sensed tachyarrhythmia, or dangerously high heartbeat rates. It is known that sometimes tachycardia, or even one or a few premature beats may induce cardiac fibrillation. It is further known that in many patients with sick sinus syndrome, exercise can produce dangerous high-rate heart irregularities. Studies have documented exercise-induced ventricular ectopy particularly in children and young adults with compete heart block. There have been a number of pacemaker designs which attempt to treat this situation, the common one being that of applying a burst of high-rate stimulus pulses to the patient's heart. Another system has been to immediately overtake the heart by delivering regular stimulus pulses at a rate higher than the observed spontaneous heartbeats.

Several prior art patents are of particular significance in providing the pertinent background of this invention. U.S. Pat. No. 3,693,626, Cole, discloses a pacer system wherein the natural rate is tracked as long as spontaneous heartbeats are occurring, i.e., the pacer keeps track are of the rate of the spontaneous beats. When the natural heartbeats cease, the pacer intervenes with a stimulus rate at or somewhat below the last detected rate, i.e., the pacing interval is only slightly longer than the interval between the last pair of spontaneous heartbeats. While this system avoids a discontinuity in heartbeat rate at the time that the pacer takes over, it does nothing to prevent discontinuities, or abrupt jumps in rate as long as spontaneous beats continue. In the U.S. Patent to Wall et al, U.S. Pat. No. 3,807,410, there is shown another analog tracking system wherein the pacer rate or escape interval is adapted to track, or follow the natural rate, and wherein the rate of returning to the fixed rate when natural beats disappear may be varied by the circuit design. However, this system likewise permits abrupt upward swings in rate without providing any control thereof.

The U.S. Pat. No. 3,857,399, to Zacouto, discloses a means of varying the pacemaker escape interval as a function of the measured time of the last cycle, but makes the escape interval dependent upon the absolute value of the spontaneous rate, and not the rate of change of the spontaneous rate. By contrast, this invention provides means for responding to the rate of change of the natural heartbeat action, including a controlled form of pacer overdrive of spontaneous pulses. The U.S. Pat. No. 4,163,451 to Lesnick et al discloses a form of immediate overdrive in view of any natural heartbeat, i.e., the pacing interval is made less than the interval of the last cycle. While such system may be useful in some particular cases, it is overly agressive for many applications. For example, it automatically causes pacer capture following a single premature ventricular contraction, or following a modest rise in the patient's pacer rate which is within a safe limit. It is desired to have a more controlled and less abrupt response which permits continuation of spontaneous heart activity under safe circumstances but yet insures pacemaker overdrive under proper circumstances.

SUMMARY OF THE INVENTION

In view of the above prior art needs, it is an object of this invention to provide a programmable cardiac pacemaker which is more optimally adaptable to sensed changes in natural rate. Specifically, it is an object to provide a programmable pacemaker which permits cycle to cycle variation of the pacing interval and escape interval subject to programmed limits on pacing rate and rate of change of pacing rate.

It is another object of this invention to provide a programmable pacer with pacing rate control, the pacing rate control having a flywheel type operation to guard against large and abrupt rate variations.

It is a further object of this invention to provide such a flywheel type pacing rate control in a pacemaker, wherein the pacer follows or tracks natural rhythms of the patient, permitting natural activity to occur so long as it is within certain absolute limits and rate of change limits. The pacemaker of this invention may be adapted for single chamber pacing only, or for dual chamber pacing.

It is a further object of this invention to provide a pacemaker which incorporates overdrive control whereby the pacemaker safely overdrives excessively high spontaneous heartbeats and then gradually returns the pacing rate to a normal, programmed, pacing rate. The pacemaker also suitably has programmable means for adjusting the rate at which the pacer overdrives and captures pacing control of the heart.

It is yet a further object of this invention to provide a programmable pacer for single or dual chamber operation having a plurality of adaptive pacing rate modes, including a flywheel mode, overdrive mode, and modified overdrive mode.

It is another object of this invention to provide a pacer having means for controlling the output current in terms of actual pacer battery voltage relative to a predetermined reference level.

In view of the above objects there is provided a pacemaker and method of operation, providing selectable flywheel and overdrive modes. In the overdrive mode the pacer decrements the pacing interval by a programmed amount following a sensed spontaneous heartbeat, whereby the spontaneous heartbeat is overtaken in controlled steps by the pacemaker. In the flywheel mode, the pacer monitors rate of change of the rate of spontaneous heartbeats, and acts to gradually change the pacing rate whenever such rate of change in either direction exceeds predetermined limits. In either mode, whenever the pacer captures the heart, the pacing rate is gradually returned to a normal programmed pacing rate. U.S. application Ser. Nos. 436,454 and 436,457, with respective different inventive entities, have been filed on the same date as this application, and are assigned to the same assignee. This application and the other two co-pending applications employ the same drawings and the same specification under the heading "Description of the Preferred Embodiment". All three applications cover inventions which are incorporated as part of the same pacemaker system, and accordingly are based upon the same environment which is disclosed commonly. The portions of the specification which are specific to the invention as claimed herein are those relating to flow charts of FIGS. 3, 3A and 4.

BRIEF DESCRIPTION OF THE DRAWINGS

FIG. 6D is a circuit diagram of an output control circuit utilized in the apparatus of this invention.

DESCRIPTION OF THE PREFERRED EMBODIMENTS

Figure 1:
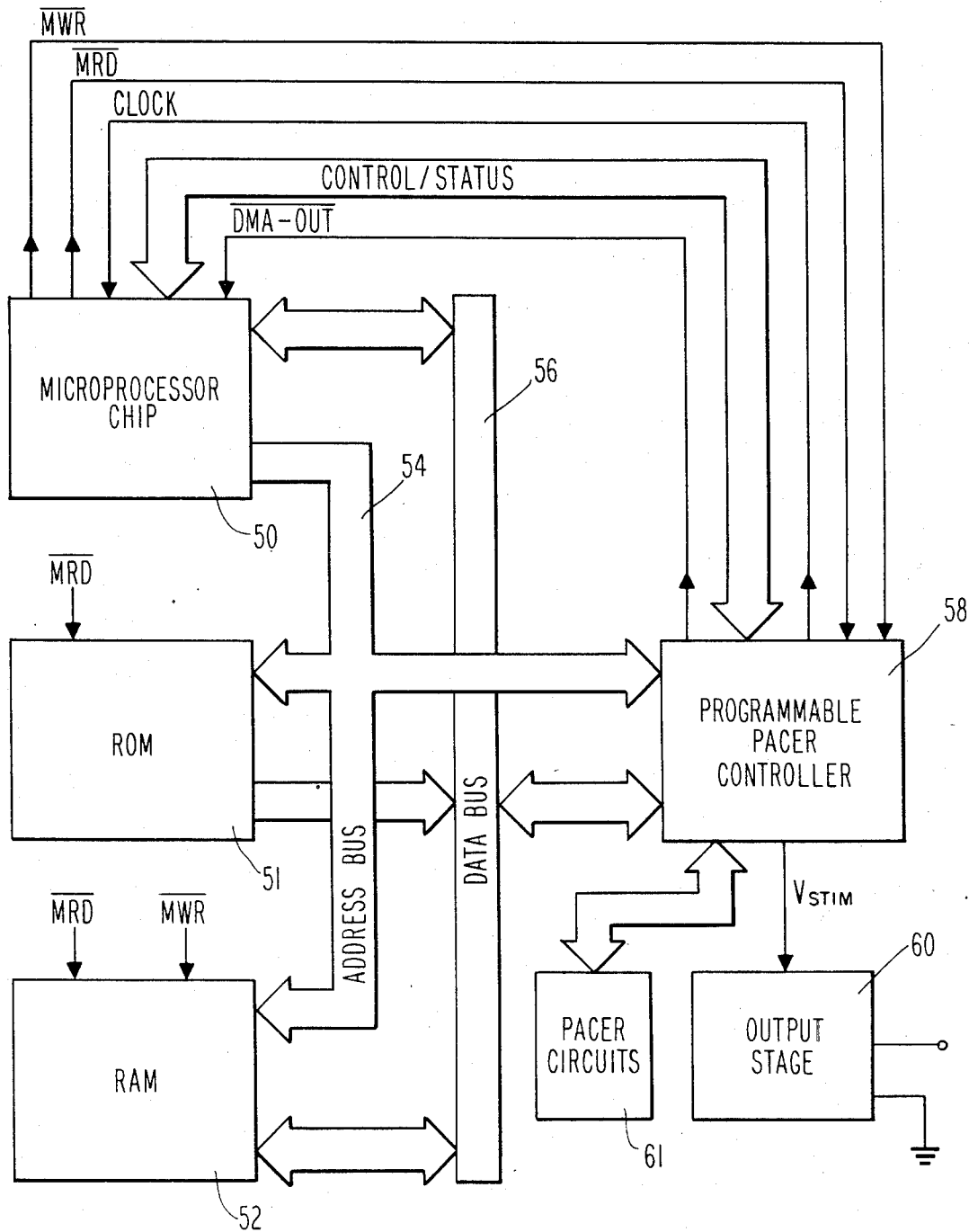
FIG. 1 is a block diagram showing the microprocessor and the primary functional blocks of the apparatus of this invention.

Referring now to FIG. 1, there is shown a block diagram of the primary components of the apparatus of this invention. Shown in block 50 is a microprocessor chip, and as used hereinafter the term microprocessor or microprocessor element means a commercially available microprocessor, whether of one or more chips. A preferred microprocessor for use in the application of this invention as part of a programmable cardiac pacer is the CDP 1802 microprocessor made by RCA. The CDP 1802, hereinafter the 1802, is fabricated on a single chip utilizing a silicon gate CMOS structure. Because of its CMOS structure it offers the design advantages of wide operating temperature range, relatively high speed, high noise immunity and in particular low power consumption. It is to be understood that particularly for an implantable pacer application, where the lifetime of the battery source is important, the low power CMOS microprocessor is particularly advantageous.

Descriptions and specifications of the CDP 1802 are freely available and in the technical literature, and accordingly a full description of the microprocessor is not necessary in this specification. However, some further comments are useful for clarifying the description of this invention. The CDP 1802 has a 40 pin circuit. A standard bidirectional parallel data bus 56 utilizes 8 pins, BUS 0–BUS 7. All parallel data communications between the CPU and external logic, memory or I/O occur via this data bus. There is an 8 bit address bus, represented by the numeral 54. All addresses must be multiplexed; the high order address byte is first outputted, followed by the low order address byte. It is to be noted that compatible memory is used with the CDP 1802 which includes address decode logic. There are 7 status flag pins, including Data Flag and Interrupt Enable Flag, 4 I/O flags and a Q Status Flag which can be set or reset directly by appropriate instructions. There are 4 timing signals, namely CLOCK, $\overline{\text{XTAL}}$, $\overline{\text{TPA}}$ and $\overline{\text{TPB}}$, the latter three being shown in FIG. 1. CLOCK is the principle timing signal, input from an external clock which in this invention is mounted on programmable pacer controller 58 and controlled by logic within that controller. The frequency of the clock may be up to 6.4 MHz, but for this application is 40 KHz. When using the on-chip clock logic of the microprocessor, an external crystal must be connected with a parallel resistor to the $\overline{\text{XTAL}}$ and clock pins. $\overline{\text{TPA}}$ and $\overline{\text{TPB}}$ are timing pulses output by the microprocessor each machine cycle, to control external logic. The remaining pins are control pin, including $\overline{\text{MWR}}$ and $\overline{\text{MRD}}$ which control memory operation, and the $\overline{\text{DMA}}$ pins which control direct memory access operation.

Still referring to FIG. 1, the address bus 54 is shown interconnected with ROM memory 51, RAM memory 52, and the programmable pacer controller circuit 58. The ROM is suitably an RCA model CPD 1833 while the RAM is suitably an RCA model CDP 1822 chip. The data bus 56 interconnects the microprocessor chip 50 with ROM 51, RAM 52 and pacer controller 58. Reference is made to co-pending EP-application S.N. 81108939.0, which describes additional detail of controller block 58, and which is incorporated by reference. Although only one ROM and one RAM block are shown, it is to be understood that there is no limitation on the amount of memory subject only to practical design considerations. As further shown in FIG. 1, the output of controller block 58, which is a timing signal represented as $V_{stim}$, is connected to a conventional output stage 60 for developing an output signal to be delivered to a patient's heart. It is to be understood that for a pacer application other circuitry is incorporated, including timing logic for determining the rate and circumstances for delivering output pulses; an input path for receiving natural heart signals and amplifying same; receiving means for receiving external program signals and modifying operating parameters in accordance with such external signals; etc. All these functions are conventional and well described in the patent literature, and are carried out either in controller block 58 or in circuitry represented by block 61 which is shown communicating with controller 58.

Referring now to FIG. 2, there is shown an illustrative flow diagram of a program routine which is run once each cycle in the pacer of this invention. This routine does not contain all steps which are carried out by the microprocessor, but contains those steps which are illustrative of the operations of the pacer which relate to the subject invention.

Figure 2A:
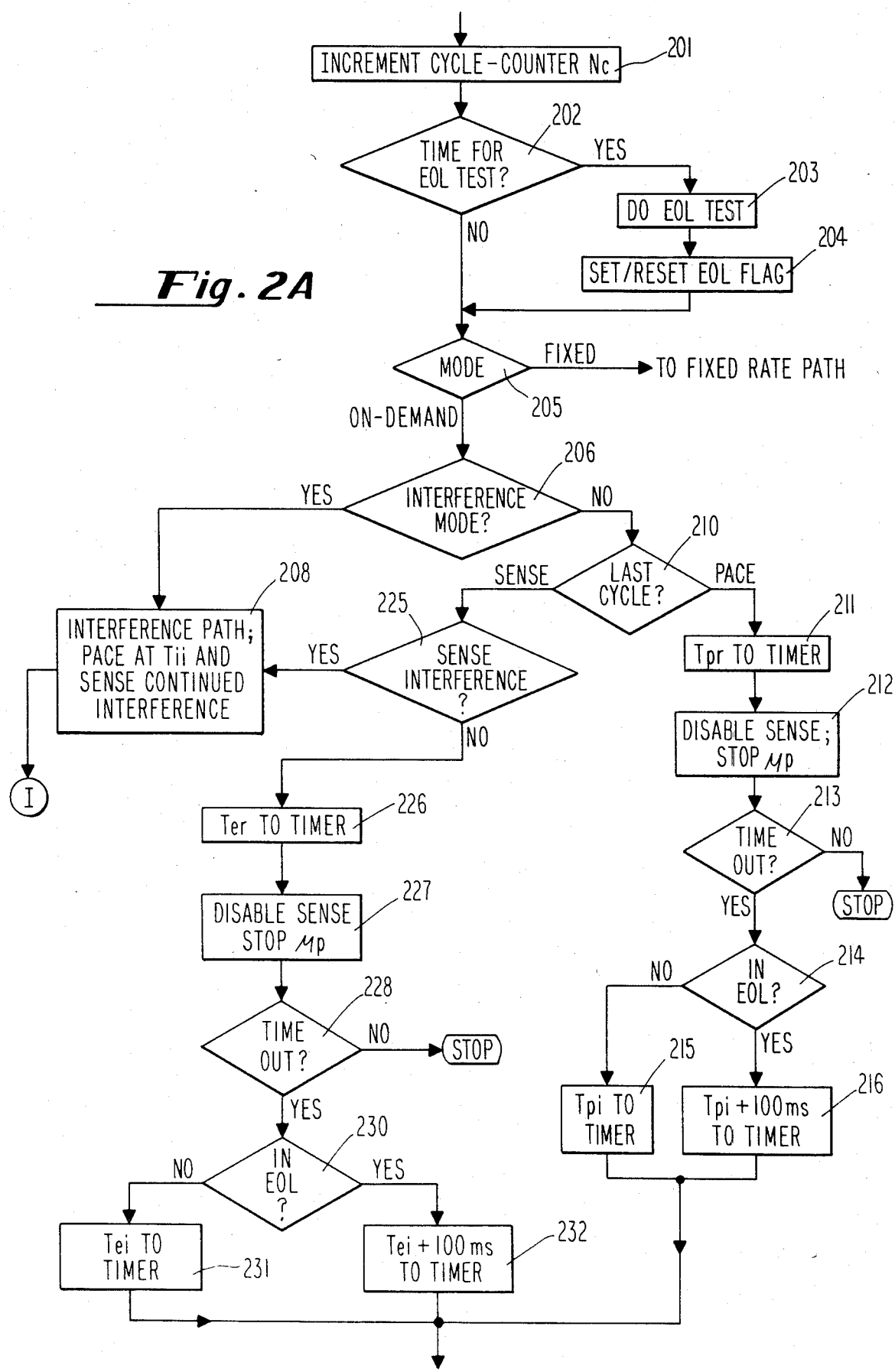
FIGS. 2A and 2B constitute a flow diagram of a simplified routine suitable for use in this invention and illustrating program control of the primary functional steps carried out each cycle.
Figure 2B:
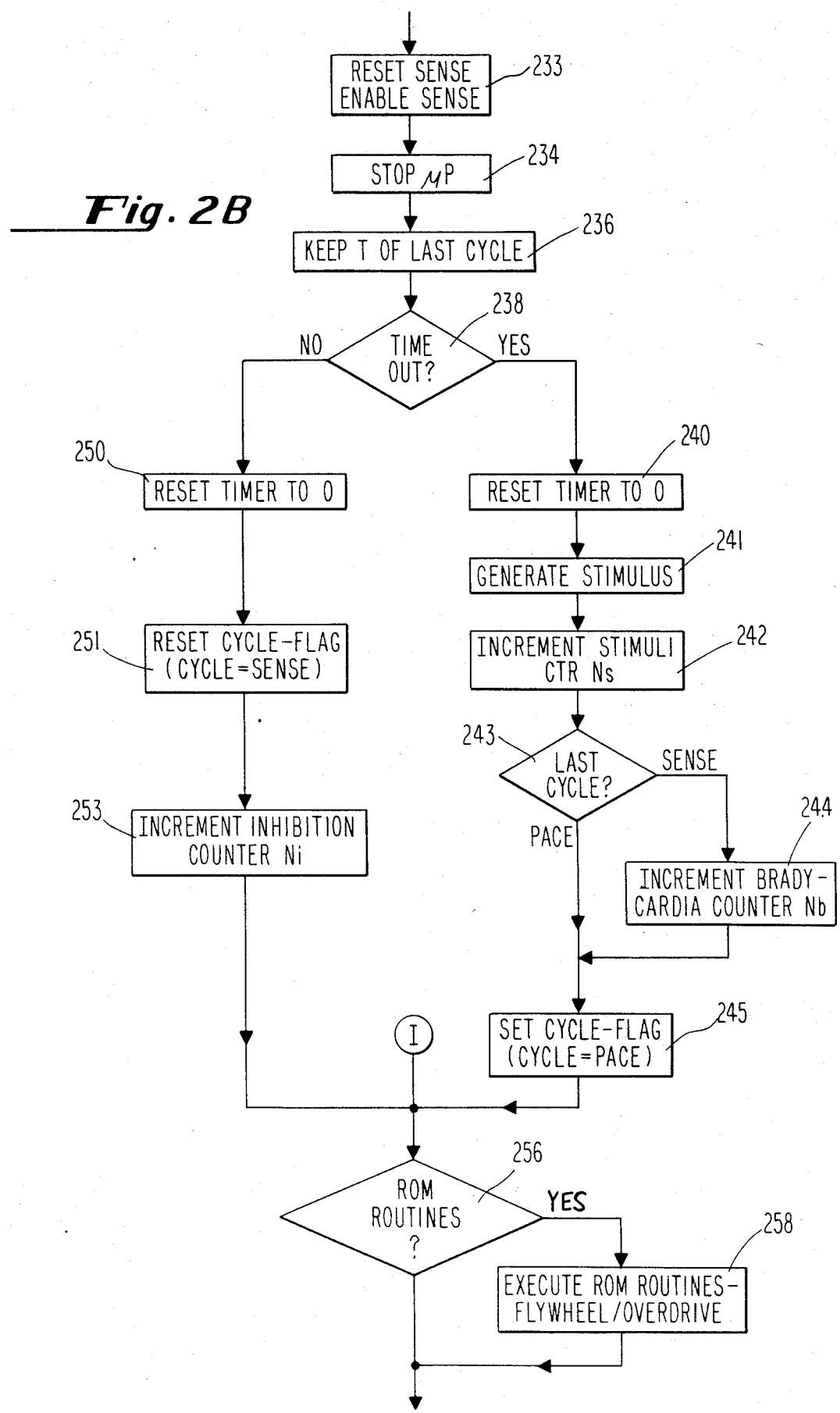

FIGS. 2A and 2B together comprise the flow diagram of the overall cycle routine which is run by the microprocessor every pace cycle. The program is stored in ROM, but many of the variables of the software-controlled operations can be re-programmed through the RAM memory.

Starting at block 201, the cycle counter is incremented, thereby providing a running count $N_c$ of the number of cycles. At block 202, the program determines whether it is time to run an end of life (EOL) test, i.e., the test is run once after passage of a predetermined number of cycles. If the answer is yes, the test is performed at block 203, and the EOL flag is set or reset at block 204 in accordance with the test result. The test is carried out by measuring the battery voltage and comparing it to a reference, the details of the test being not pertinent to this invention. Following this, at block 205, it is determined whether the pacer is in a "fixed" rate mode or is operating "on-demand". If it is in fixed rate mode, the program branches to a separate fixed rate path which is not shown. The following portion of the flow diagram illustrates the primary components of the on-demand path.

At block 206, the program determines whether the pacer is in an interference mode, by checking data generated during the last cycle. If it is found that the pacer is in the interference mode, the path branches through block 208, designated Interference Path. The details of this path are not included, but basically this path senses whether interference has continued, and causes the pacer to pace at a special programmed rate having an interval $T_{ii}$. At the end of the interference path the program branches, as shown at the output I, to the bottom of the cycle routine as seen at the bottom of FIG. 2B.

If the pacer is not in the interference mode, a determination is made at block 210 as to whether the last cycle ended with a pace pulse or a sensed heartbeat. For a pace pulse, the right hand branch is taken. At block 211 the timer, which was reset to zero near the end of the last cycle, is set to time out after an interval $T_{pr}$, the pacing refractory interval. The manner of setting the timer, the timer circuitry and the manner of communicating a time out condition back to the microprocessor is discussed in detail hereinbelow. For purposes of the flow diagram, it is assumed that timing operations are carried out by conventional circuitry external to the microprocessor, utilizing circuitry on the controller chip 58 which is in communication with the microprocessor chip 50. Following setting the time out interval, at block 212 the microprocessor generates a signal which is outputted through controller 58 to disable the sensing circuitry, and to cause the microprocessor to be stopped. During the time that the microprocessor is stopped, clock signals from controller 58 are not transmitted to the microprocessor chip 50, thereby saving the power that would otherwise be required to operate the microprocessor.

In normal operation, the microprocessor is started again when the timer times out due to elapse of the interval $T_{pr}$, causing clock pulses to be gated to the microprocessor, thereby starting its operation again. At block 213, it is determined whether the microprocessor was started by a time out of the timer, which would be determined by checking an appropriate status signal inputted from controller 58 to the chip 50. Assuming a proper time out, meaning that the refractory interval has ended, the program goes to block 214 and determines if pacer operation is in the EOL mode, by checking the EOL flag as determined at block 204. Assuming no EOL operation, at block 215 the programmed pacing interval time $T_{pi}$ is transferred from the microprocessor to the timer, so that another output signal is generated by the timer when it reaches the value $T_{pi}$.

Note that at this point the timer is not reset, but rather the controller circuit is programmed to produce another signal when the timer reaches the value $T_{pi}$. If the pacer is in EOL mode, the program branches to block 216 where the pacing interval is set at the programmed $T_{pi}$ value plus 100 ms, thereby causing a reduced rate of operation during EOL conditions. This technique results in reduced power drain after EOL has been detected, due to the lower rate of producing pacing pulses.

Returning to block 210, if the last cycle was determined to have terminated with a sensed heartbeat, the program proceeds to the left path. At block 225, a series of instructions are carried out over a period of time which is less than the refractory interval, to determine whether interference is still present. If the answer is yes, the program branches to block 208 to continue the cycle. Assuming no interference, the program proceeds to block 226, where the timer is loaded with $T_{er}$, the escape refractory interval. Following this, at block 227, the sense circuitry is disabled, since the pacer is within the refractory interval, and the microprocessor is stopped and stays stopped until started again by a signal from controller 58. When started again, the program determines, at block 228, whether there has been a time out of the escape refractory interval. Assuming so, at block 230 the program checks to see if the pacer is in the EOL mode. If not, the program value of the escape interval, $T_{ei}$ is sent to controller 58 at block 231, to cause a timer output when it times out such interval. If the pacer is in EOL, the escape interval is enlarged by 100 ms, as shown in 232.

Continuing the program flow chart, as seen in FIG. 2B, the pacer resets and then enables the sense circuitry, as designated at block 233. This is done since the refractory interval has now been timed out, and the pacer is to be enabled so as to sense a natural heartbeat. Following this the microprocessor is stopped at 234, by sending a status signal to controller 58 which causes opening of the return path which connects clock signals to the microprocessor chip 50. While the microprocessor is thus off, the timer is timing out the escape interval. During this time, a received natural beat will be processed on controller 58 to generate a status signal and restart the microprocessor, and likewise a time out of the timer will again start the microprocessor. After the program resumes, the time T of the last cycle is obtained from controller 58 and stored, for later use in the routine illustrated in FIG. 3. At block 238 a determination is made as to whether there has been a time out, by checking the status signals from controller 58. If yes, a stimulus pulse is to be delivered and the program takes the right hand path. If no, logic indicates that a spontaneous heartbeat has been received and the program takes the left hand path.

Assuming a time out, the timer is reset to zero at block 240, and at block 241 the program causes transmission of the necessary information to controller 58 to cause generation of an output stimulus pulse, or a series of pulses. This is suitably done by utilizing the DMA mode of the microprocessor, as described in co-pending EP-application No. 81108939.0. At block 242 a stimulus counter is incremented, to keep a running total of delivered stimulii, $N_s$. At block 243, the program recalls whether the last prior cycle had ended with a sense or a pace by checking the cycle-flag. If the answer is sense, this means there has been a transition to pace due to the absence of a natural pulse during the escape interval, and at block 244 a bradycardia counter is incremented, to keep a running total $N_b$ of such events. Following this, at block 245 the program sets the cycle flag to indicate that the last cycle terminated in a delivered pace pulse.

Returning to block 238 and taking the left hand path, corresponding to a received QRS, the timer is reset to zero at block 250 and at block 251 the cycle flag is reset to indicate that the last cycle terminated with a sensed heartbeat. At block 253, an inhibition counter is incremented to keep a tally $N_i$ of such inhibition events.

At the bottom of FIG. 2B, the three above described paths are joined, together with the fixed rate path which is not illustrated, and it is determined whether the pacer is programmed to carry out additional routines stored in ROM 51. If yes, the program branches through block 258 to execute those ROM routines, which include the flywheel/overdrive routine illustrated in FIG. 3.

The above flow chart description has made frequent reference to setting and resetting the timer, determining when the timer has reached a set value, and starting and stopping the microprocessor. Such operations may be carried out entirely by software, or software-controlled hardware. For the preferred embodiment of this invention, the control circuitry for carrying out these functions is located on a chip which houses controller 58 and which, as seen in FIG. 1, is interconnected with the microprocessor and memory by the address bus 54, data bus 56 and control lines which are connected to the microprocessor chip 50. The pertinent details of the programmable pacer controller (PPC) are discussed in connection with FIG. 5.

Figure 3:
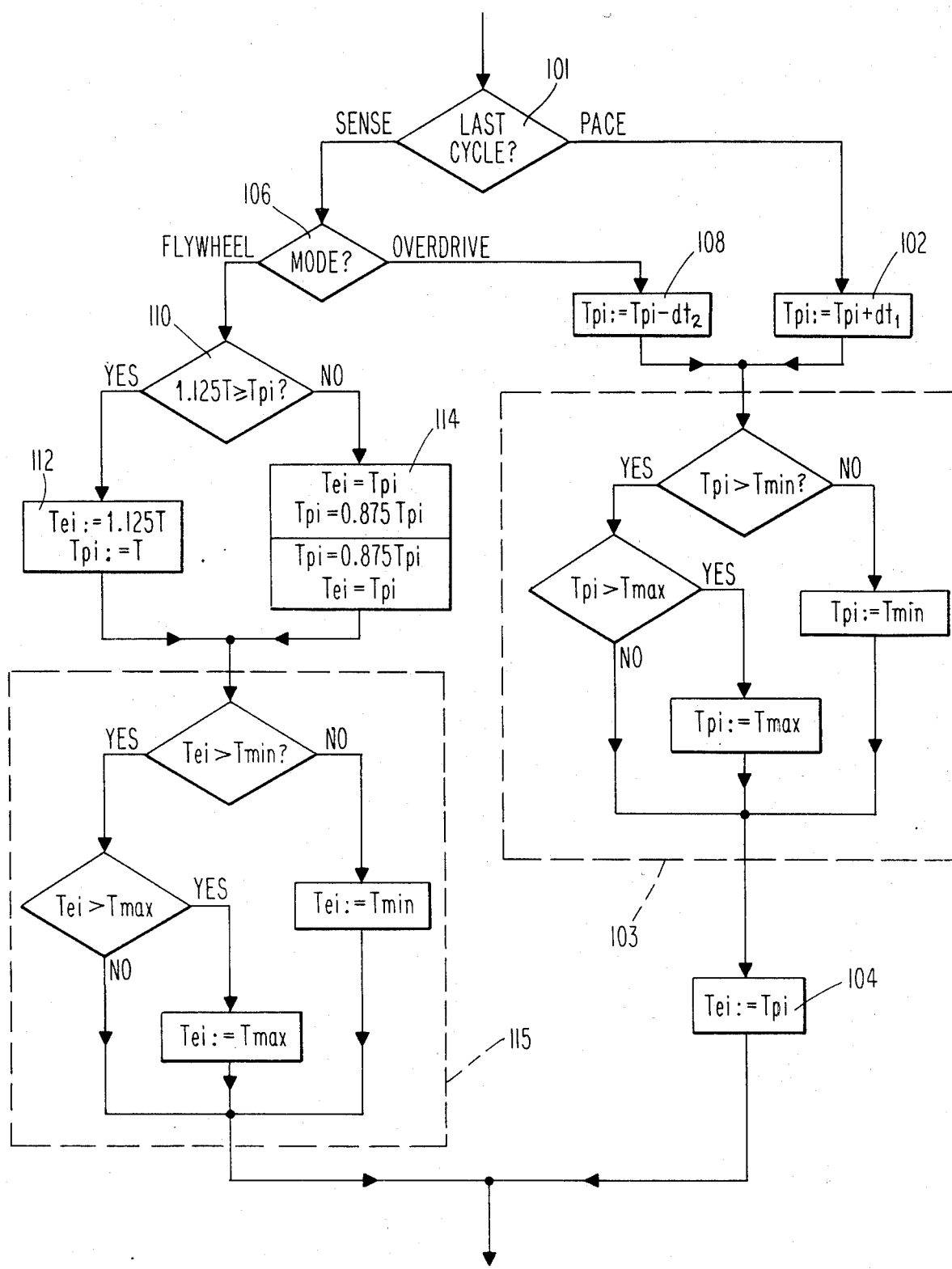
FIG. 3 is a flow diagram of a subroutine for carrying out the specific steps of the preferred embodiment of this invention.

Referring now to FIG. 3, there is shown a flow diagram of the specific routines used in the microprocessor of this invention, which carry out the flywheel and overdrive modes. This flow diagram is illustrative of the invention as applied to a single chamber pacer, e.g. VVI or AAI. The invention is also applicable in a dual chamber pacer, as discussed in connection with FIG. 3A.

The program first checks memory at block 101 to determine whether the last cycle ended with a pace pulse, or a sensed heartbeat, this information having been stored as illustrated in FIG. 2. If the result of the inquiry is pace, the routine branches to the right hand branch which provides for incremental reduction of the pacing rate until it reaches the normal program rate, corresponding to $T_{max}$. The first step at block 102 is to increment the pacing interval by $dt_1$, suitably one or two ms. The value of $dt_1$ is a programmed variable, and may suitably range from about 0.5 ms to 10 ms. It is to be noted that in incrementing $T_{pi}$, the pacing rate is being decreased, and in the absence of natural heartbeats the rate decreases slowly from cycle to cycle until it reaches the normal program rate. In this manner, when the pacemaker recaptures pacing of the heart following a series of spontaneous heartbeats, the pacing rate is gradually decreased from the tracked natural rate down to the programmed rate. After incrementing $T_{pi}$, a series of checks are performed at blocks 103 to make sure that the pacing rate is neither below nor above the permissable pacing rate. First $T_{pi}$ is compared with $T_{min}$. If it is found that $T_{pi}$ is not greater than $T_{min}$, $T_{pi}$ is set equal to $T_{min}$. If $T_{pi}$ is greater than $T_{min}$, it is then compared with $T_{max}$. If $T_{pi}$ is greater than $T_{max}$, it is set to the value of $T_{max}$. In either case, the escape interval $T_{ei}$ is then set equal to $T_{pi}$ at block 104 since there is no hysteresis during pacing.

If at the first decision block 101 the pacer determines that the last cycle was ended by a sensed heartbeat, the program, at block 106, next makes the determination of whether it is in the flywheel or overdrive mode. This information is stored in memory, having been entered by normal programming techniques. If the mode determination is overdrive, then the next step at block 108 is to decrement $T_{pi}$ by an amount $dt_2$, which is suitably 50 ms but may be in a range of about 5–100 ms, or more. Decrementing $T_{pi}$ has the effect of increasing the pacing rate, for the purpose of overdriving the natural rate of the heart. It is to be remembered that at this point, since the last cycle ended with a sensed hearbeat, the effective rate was greater than the pacing rate at which the pacer was then operating. Thus, in the overdrive mode, the pacer immediately moves toward a higher pacing rate so as to overtake and overdrive the heart. It is to be noted that $dt_2$ may be set at a value sufficiently small such that in most cases the pacer does not overdrive in the first succeeding cycle. This may have the advantage of avoiding overdrive in the event of a single premature heartbeat, or perhaps even several, in a patient situation where this is desirable. For example, if a sensed spontaneous beat has jumped upward in rate corresponding to a decrease in cycle interval of more than 100 ms, and $dt_2$ is set to 50 ms, it will take at least three cycles before the pacer overdrives the heart, assuming that the heart rhythm stays at the same high rate. However, if the spontaneous heart activity ceases after a single spontaneous beat, the pacing rate is raised only by an amount corresponding to a reduction of the pacing interval by 50 ms, meaning that the resulting pacing rate decreases back to the programmed rate much more quickly, and pacing at the high rate corresponding to the single irregular beat is avoided. Of course, for a patient whose history indicates desireability of overdriving as quickly as possible, $dt_2$ may be programmed to a high value.

When the pacer is in the flywheel mode, the first determination at block 110 is whether the last cycle interval T has changed compared to the prior interval, by more than a predetermined amount. In the program as illustrated, the flywheel rate of change limit is set at 12.5%, meaning that a change of rate up or down by more than this factor is outside of the programmed range. Although 12.5% has been used in the example of this specification, it is to be understood that the exact values of the change of rate limits are design parameters, and the ±12.5% range is illustrative only. Further, it is to be understood that the limits on upward and downward rates of change may be different, and are not necessarily equal as here illustrated.

Still referring to the illustrated embodiment of FIG. 3, if the measured value of T for the last cycle is such that 1.125T is greater than or equal to $T_{pi}$, this means that the rate has either increased by less than 12.5% or has in fact dropped. For this condition, the program takes the "yes" branch, and at block 112 sets the escape interval equal to 1.125T, and sets $T_{pi}$ equal to T. Thus, the 12.5% factor is established as a hysteresis differential, or factor, and if during the next cycle no natural pulse is received during time equal to 1.125T of the last interval, then a pacing pulse is delivered. Also, by setting $T_{pi}$ equal to T, the pacing interval and thus the pacing rate are caused to track the cycle-to-cycle changes in T.

If it is determined that 1.125T is greater than or equal to $T_{pi}$, than the "no" branch of the flywheel path is taken. The next step, at block 114, has two alternate options, either one of which may be utilized in the pacer of this invention. In the first option, the escape interval is set equal to the pacing interval during the prior cycle, and then the pacing interval is decremented so that it is 0.875 $T_{pi}$, i.e., it is decremented by 12.5%. Thus, where the spontaneous rate has increased by 12.5% or more, the pacing rate is increased by only 12.5%. Stated differently, for natural heartbeats having upward rate changes of more than the limit on the rate of change, the pacing rate is permitted to rise only by the predetermined maximum rate of change, which in this example is 12.5%. In the alternate option, the pacing interval is first set to 87.5% of its prior value, and then the escape interval is set equal to the pacing interval. In option 2, it is seen that the escape interval is reduced a cycle earlier, such that the pacer more aggressively adapts to capture heart pacing.

After either alternative route which is taken following the interval comparison, a check is made at 115 to see whether the escape interval is within the minimum and maximum program limits. The escape interval is first compared to $T_{min}$, and if it is found to be less than $T_{min}$ it is set equal to the value of $T_{min}$. If it is greater than $T_{min}$, then it is compared to $T_{max}$, and if found greater than $T_{max}$ it is set equal to the value of $T_{max}$.

Figure 3A:
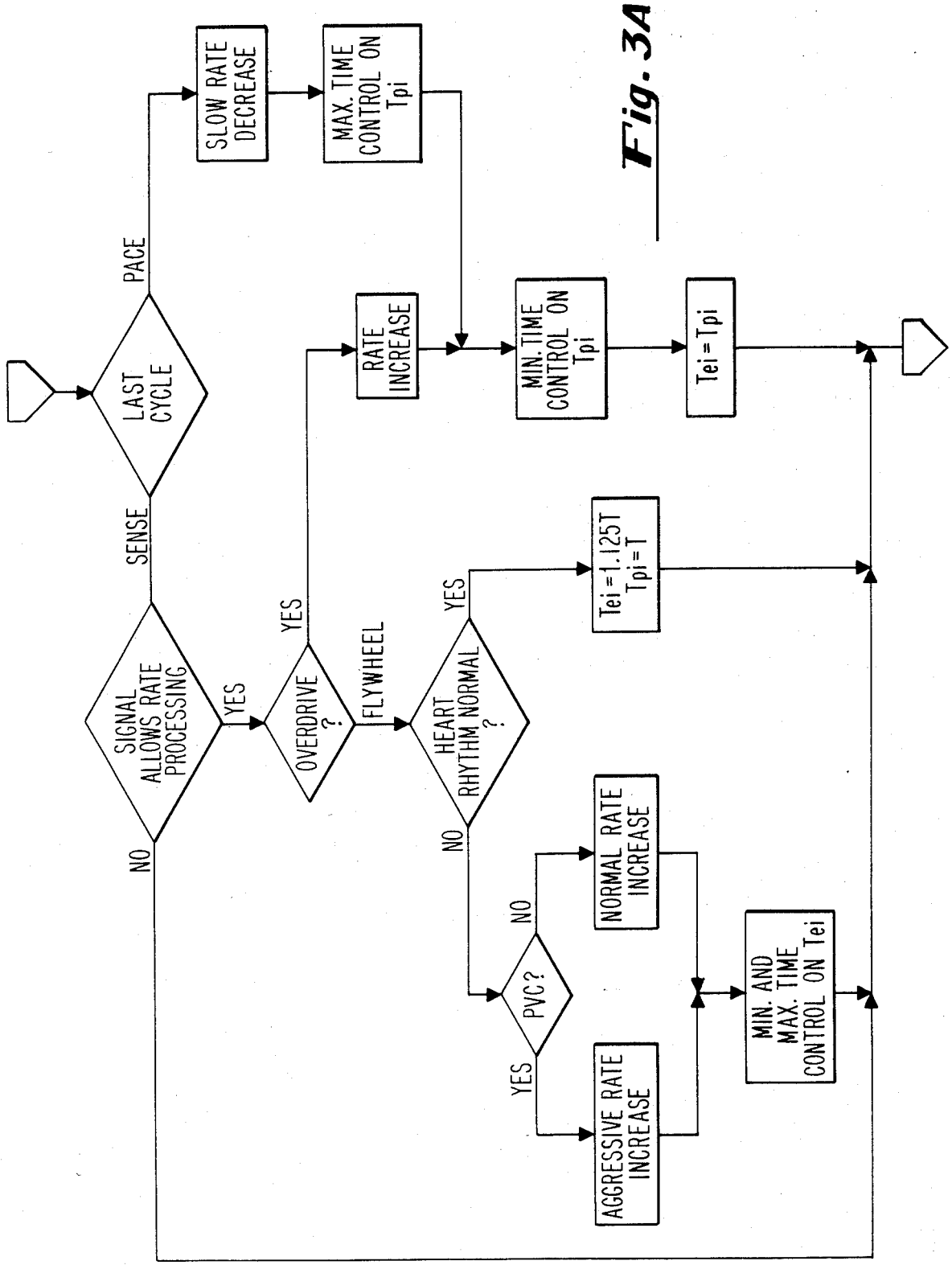
FIG. 3A is a flow diagram illustrating a modification of the subroutine of FIG. 3 for use in a dual chamber pacer.

Referring to FIG. 3A, there is shown an alternate flow diagram of the rate control subroutines for a dual chamber pacemaker, e.g. a DDD type. For this embodiment, atrial timing is controlling, and the pacer recycles on the atrial beat or on a PVC (sensed ventrical beat not proceeded by an atrial beat). Starting at the top of the subroutines, if the last cycle was a pace cycle, the pacer causes a slow rate decrease and imposes a maximum time control on $T_{pi}$, as at blocks 102 and 103 of FIG. 3. If the last cycle is determined to have been a sense cycle, i.e., either sensed A or PVC, the pacer determines whether rate processing is allowed. No rate processing is allowed if the rate is above the predetermined maximum limit, i.e., tachycardia is present. If no, the subroutine skips to the end, but if the answer is yes there is a determination of whether the pacer is in the overdrive or flywheel mode. If in the overdrive mode, the rate is increased, the minimum time on $T_{pi}$ is controlled and $T_{ei}$ is set equal to $T_{pi}$, as at blocks 108, 103 and 104 of FIG. 3. In the flywheel mode, it is first determined whether the heart rhythm is normal, i.e., is it within given limits as illustrated at block 110 of FIG. 3. If yes, then $T_{ei}$ is set equal to 1.125 T and $T_{pi}$ is set equal to T, as at block 112 of FIG. 3. If no, the pacer determines whether there has been a premature ventricular contraction (PVC). If no, the normal rate increase is processed, i.e. $T_{ei}=T_{pi}$ and $T_{pi}=0.875\ T_{pi}$. If there has been a PVC, then the aggressive rate increase is chosen, i.e. $T_{pi}$ is 0.875 $T_{pi}$ and $T_{ei}=T_{pi}$. The subroutine concludes by imposing the minimum and maximum time controls on $T_{ei}$.

Figure 4:
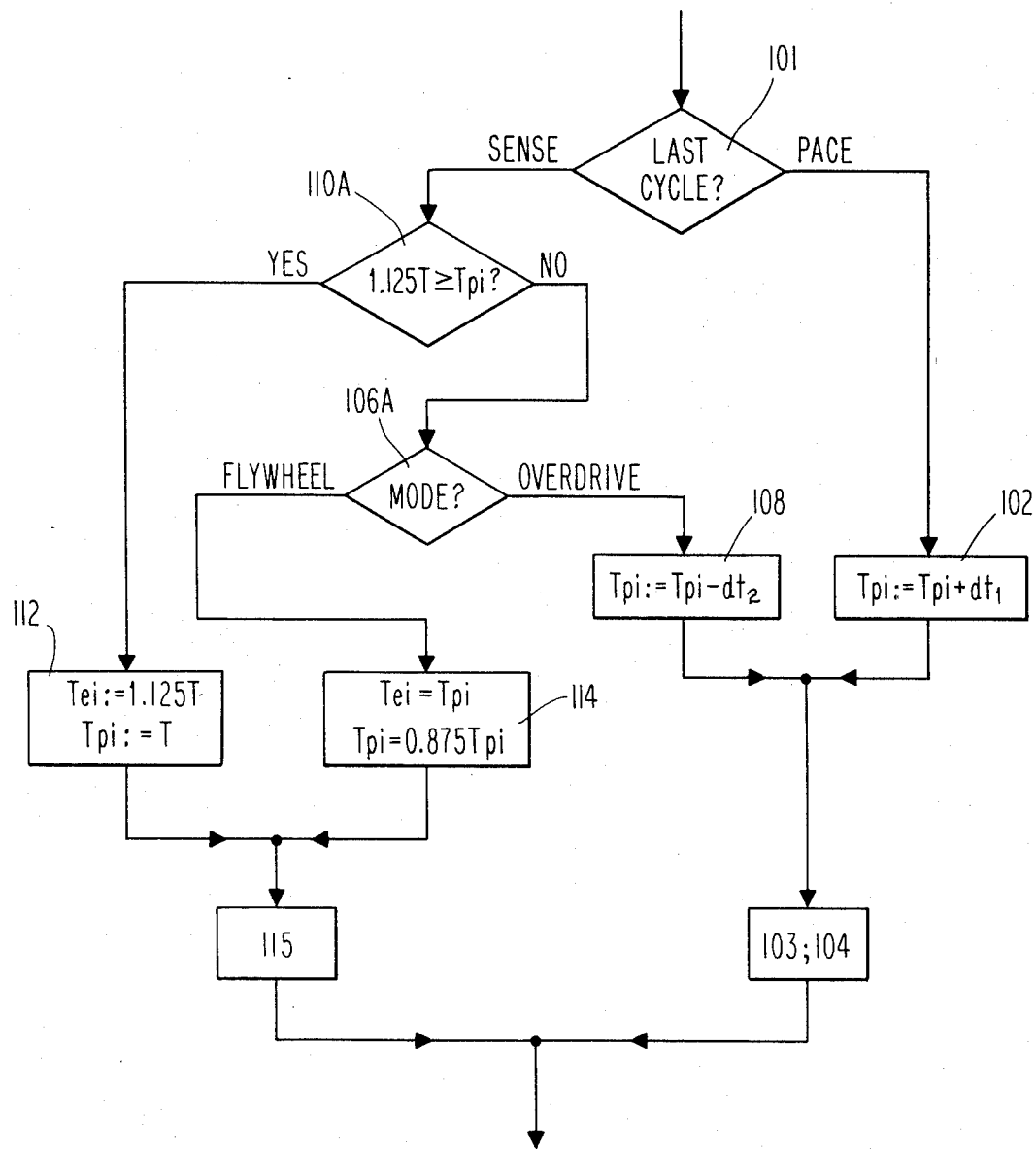
FIG. 4 is a flow diagram of a subroutine for carrying out an alternate embodiment of this invention.

In an alternative arrangement embodied in the flow diagram of FIG. 4, the mode decision block and the interval comparison block are interchanged compared to the diagram of FIG. 3. As seen, following determination that the last cycle ended with a sensed heartbeat, the measured time interval is first compared to the last adjusted pacing interval at block 110A. Here, as with the embodiment of FIG. 3, if 1.125T is greater than the pacing interval, the program branches to the flywheel path which sets the pacing interval equal to T and sets the escape interval at 12.5% higher than the last measured interval. However, if the last interval is reduced by more than 12.5% compared to the pacing interval for that cycle, then the program makes the choice of flywheel or overdrive mode at 106A, in accordance with programming information which has been inputted to the memory. Thus, in this arrangement, even when the overdrive mode is chosen, it is utilized only when the pacing rate has increased in rate more than the programmed limit, e.g. 12.5%. Thus, this hybrid arrangement permits natural beats to continue as long as the change in rate does not exceed 12.5%, from cycle to cycle, but goes into overdrive when the change in rate does exceed that limit. Alternately, although not shown in FIG. 4, the pacer may be placed in overdrive upon the occurrence of a natural beat or beats at a rate in excess of a predetermined rate, but less than the maximum rate. Thus, for example, if the maximum rate allowed by the pacer is 120 bpm, the pacer may be programmed to go into overdrive any time a rate in excess of 90, 95, 100, etc. is sensed.

There is thus shown a highly flexible and programmable system, which monitors the timing of spontaneous beats and adjusts the pacer escape interval and pacing interval accordingly, constraining such adjustments to changes which are within predetermined limits. Whenever the pacemaker takes over and delivers a stimulus pulse following timing out of the escape interval, the pacing rate is then decreased in small increments until either spontaneous beats occur or the pacing rate has returned to the programmed minimum rate. As long as the sensed heartbeat has arrived within an interval which represents a change from the pacing interval which is within a predetermined range, the pacer generates a pacing interval which tracks the sense interval, so that when pacing is resumed it is at the last measured spontaneous rate. If the patient's natural rate jumps up by more than a programmed percentage rise, then the pacer either goes into overdrive and captures the heart relatively quickly, or increases the pacing rate in predetermined increments set by the flywheel path. Thus, by programming the rate of change limits, as well as the overdrive and flywheel incremental changes in pacing interval, a great deal of flexibility is given to adapting the pacer response in accordance with patient history and needs.

While the invention has been described in terms of cycle-to-cycle comparisons of cycle intervals, the invention embraces more complex comparisons for which the microprocessor may be programmed. For example, a series of 2 or more successive intervals T may be averaged, with the average compared with the interval next preceeding the series, or with the prior series, to determine whether rate or change of rate has exceeded predetermined limits. As can be extrapolated from this example, other similar manipulations may be employed in judging the abruptness of rate change and thus determining whether the pacer tracks the spontaneous rate or adapts to overtake and capture the heart. Likewise, at block 114 of the flywheel path, $T_{ei}$ may be set to be only a fraction of $T_{pi}$, so as to provide a form of overdrive. Also, both the flywheel and overdrive path may be utilized in atrial or AV sequential modes. In an AV pacer, the pacer may branch to the right if a ventricular signal preceeds any atrial signal.

Figure 5:
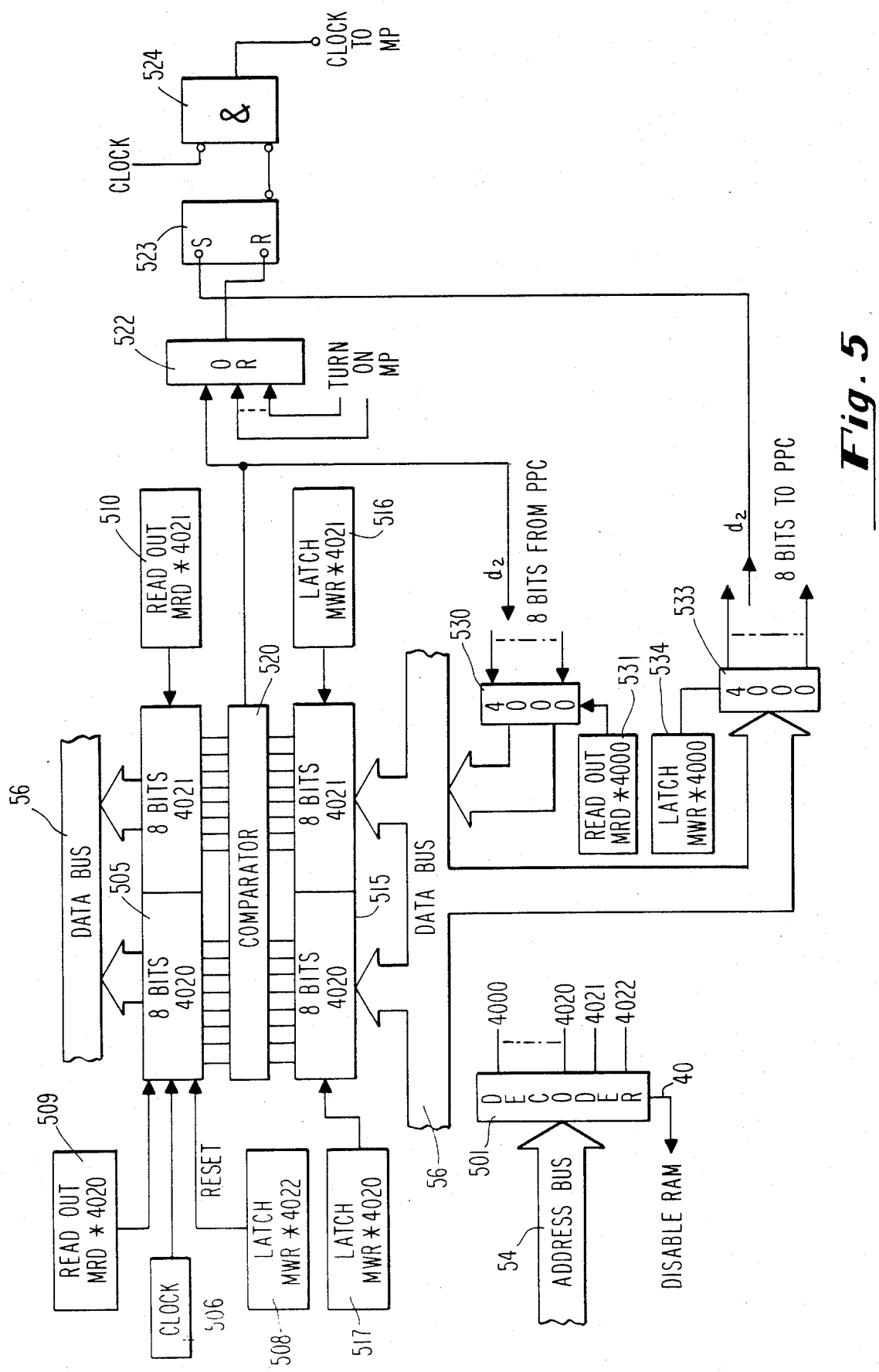
FIG. 5 is a detailed diagram of important components of the programmable pacer controller 58.

Referring now to FIG. 5, there is shown a detailed diagram of pertinent portions of the controller 58. The address bus 54 is connected to decoder 501 to determine whether a memory location of the controller memory has been properly addressed, providing a high output on a line corresponding to the decoded address. The data bus 56 is connected to a 16 bit register and latch 515, shown divided into 2 8 bit registers addressed as 4020 and 4021. The gating of a decoded 4020 address signal with an MWR pulse (as illustrated at block 517) causes latching of data from bus 56 into register 4020; likewise 4021 and MWR (illustrated at block 516) cause writing of data into 4021. A divider claim 505 is shown separated into an 8 bit register addressed as 4020 and an 8 bit register addressed as 4021. Clock 506, suitably operating at 40 KHz, inputs clock pulses to 505 to cause it to operate as a binary up counter. Data from 505 can be read onto the data bus upon software control, by the gating of an MRD signal and either the 4020 or 4021 address, as illustrated at 509, 510. Also, counter 505 is reset by the microprocessor by putting 4022 on the address bus and outputting a MWR pulse. The counter outputs are connected to a first series of inputs of magnitude comparator 520, and a second set of inputs to comparator 520 are connected to the latches associated with register 515. If the counter content is equal to or greater than the content in the respective latched line from 515, a timer output is generated, resulting in a signal which is used to activate the microprocessor in order to take a designated action, e.g., restarting it.

The latching of data from 515 under control of the microprocessor through a memory write cycles provides the means of setting the timer to a programmed value of T; the counter, and thus the timer is reset by a memory write instruction addressed to location 4022. The contents of the timer can be read by a memory read instruction addressed to 4020, 4021, which places one of the 8 bit words from register 505 onto the data bus. The output of the timer, taken from comparator 520, is connected to OR circuit 522, the output of which is connected to the reset input of flip flop 523. The output 523 is inverted and connected to a first input of AND gate 524, which receives clock pulses at its other input. It is seen that a high signal to gate 522 enables gate 524, thus starting the microprocessor by connecting clock pulses to it, as happens when the timer times out to the programmed value set into register 515. The microprocessor can also be turned on by other events detected by the controller which cause a high signal on one of the other inputs to gate 522. The microprocessor is turned off by an instruction which sets flip flop 523.

The status of the pacemaker can be controlled by a microprocessor-generated "status" word, and conversely a status change due to a time-out or other external influence can be interrogated by the microprocessor by tracing the "status flag" set when the microprocessor was activated. The status control word is written by addressing location 4000, shown at block 533, the word being latched in as indicated at 534 by the MWR instruction.

The 8 bits of the status control word are connected as separate control signals to different controller points, to provide these controller functions:
$d_0=0$: clear and disable "Vsense"
$d_1=0$: clear and disable "Asense"
$d_2=0$: continue $\mu$P-clock $\alpha$P
$d_3=0$: disable d.v.m. time-out
$d_4=0$: continue normal S0/S1 mode $\mu$P
$d_5=0$: disable ext. input to activate $\mu$P
$d_6=0$: no reset on external E.O.L.-detector
$d_7=0$: disable transceiver/modem
$d_0=1$: enable "Vsense" to activate $\mu$P
$d_1=1$: enable "Asense" to activate $\mu$P $d_2=1$: stop μP-clock
$d_3=1$: enable d.v.m. time-out
$d_4=1$: set DMA mode for pulse-generating
$d_5=1$: enable ext. input to activate μP
$d_6=1$: reset external E.O.L.-detector
$d_7=1$: enable transceiver/modem Note, for example, that when the $d_2$ bit is high circuit 523 is reset, thus stopping the microprocessor clock. Status flags are read with an MRD instruction (block 531) at block 530, which is addressed as 4000. The inputs to block 530 are derived from separate controller points, and represent the following status conditions:

$d_0=0$: no "Vsense" activity
$d_1=0$: no "Asense" activity
$d_2=0$: counter content<time out value
$d_3=0$: no d.v.m.-activity
$d_4=0$: no data from modem
$d_5=0$: no external activity
$d_6=0$: before E.O.L.-point
$d_7=0$: no modem-error
$d_0=1$: "Vsense" activity
$d_1=1$: "Asense" activity
$d_2=1$: counter≧time out value (i.e.: "time-out")
$d_3=1$: d.v.m.-time out
$d_4=1$: modem: data ready (on parity bit)
$d_5=1$: external activity
$d_6=1$: after E.O.L.-point
$d_7=1$: modem: no-receive/error Note, for example, that time out causes a high signal from comparator 520, which is connected to the $d_2$ bit of register 530.

The arrangement of controller 58, as illustrated in FIG. 5, thus provides means for turning the microprocessor on and off; it is turned off by a microprocessor MWR instruction, and turned on by a condition sensed by the controller. Following turn on, the microprocessor can read the status word to determine exactly what was the cause of the turn on. By this means, and proper programming, the microprocessor is operated in an optimally efficient, energy-saving manner. As seen in the flow chart of FIGS. 2A and 2B, the microprocessor is turned off at several points in each cycle of the periodic routine, e.g., waiting for time out of the refractory period, and then waiting for time out of the remaining pacing interval. By such programming and utilization of softwarecontrolled controller hardware, the microprocessor is on less than 25% of the time, and preferrably only about 15-20% of the time. This is important in allowing a clock rate of 40 KHz or more, which rate enables very precise generation timing signals. Although 40 KHz is the preferred rate, rates of 10 KHz to 100 KHz may be used.

Figure 6A:
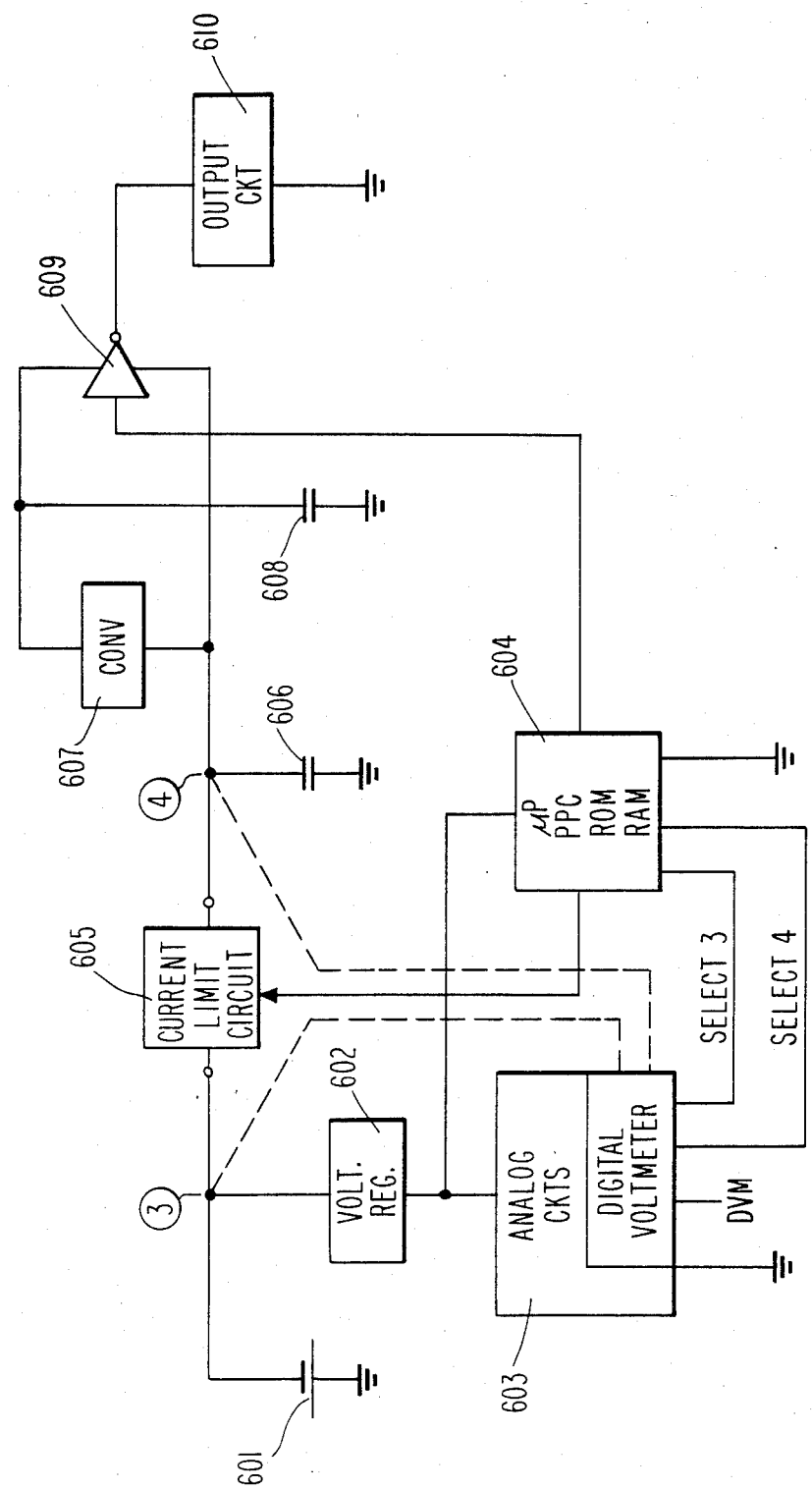
FIG. 6A is a circuit diagram illustrating connection of power to the circuit portions of the pacer of this invention.
Figures 7A, 7C:
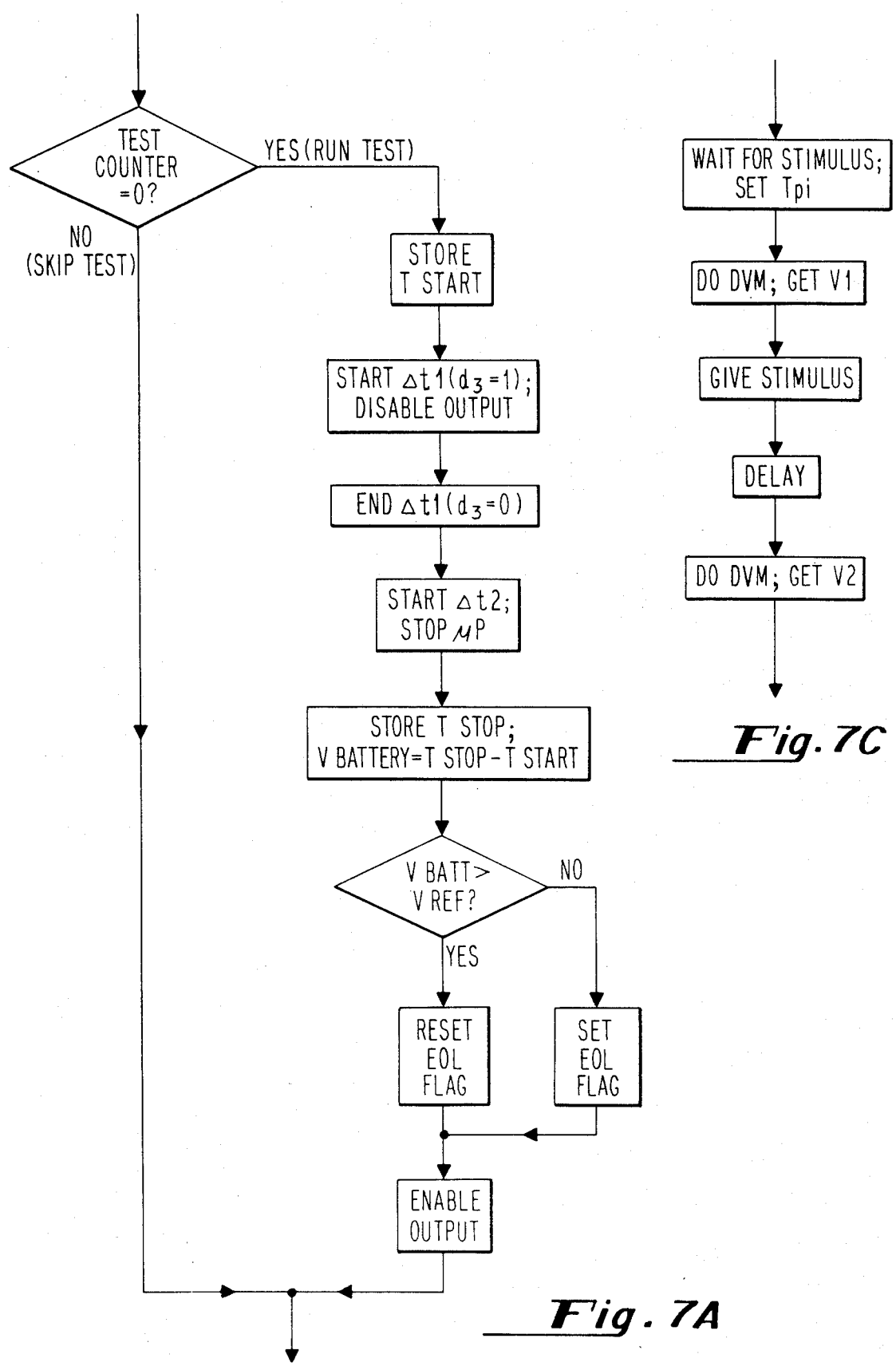
FIG. 7A is a flow diagram of the program for carrying out a first end of life test.
FIG. 7C is a simplified flow diagram of the program for testing pacer lead impedence.
Figure 7B:
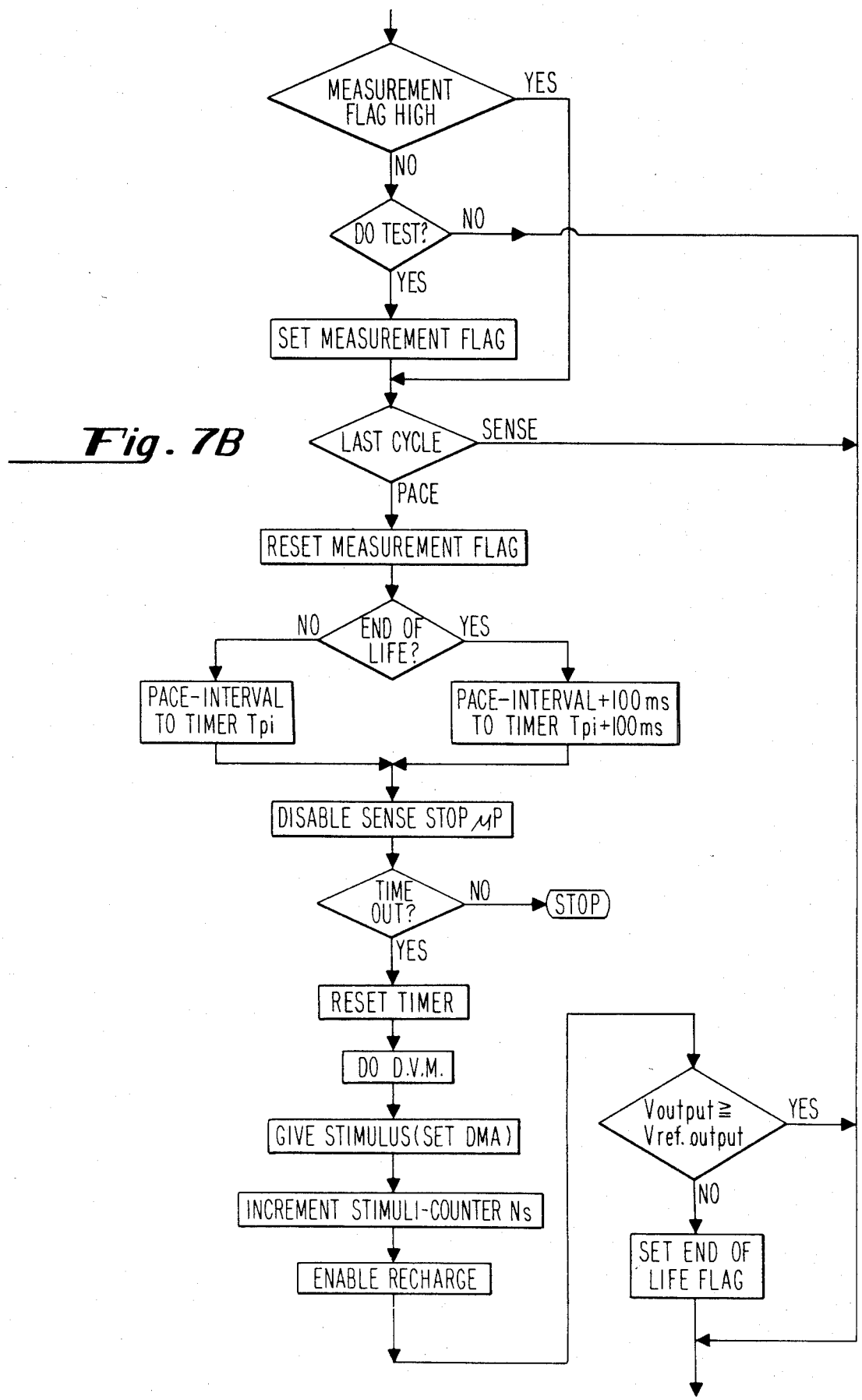
FIG. 7B is a flow diagram of the program for carrying out a second end of life test.

Turning now to FIG. 6A, there is illustrated a circuit diagram of the pacer of this invention, showing certain features pertinent to maintaining proper voltage or current to critical parts, and to the tests which are illustrated in FIGS. 7A, 7B and 7C. Power is supplied by battery 601, having an output terminal connected to point 3. Voltage regulator 602 is connected to point 3, and provides a regulated voltage to analog circuits 603, and the microprocessor-memory-controller elements indicated at block 604. The microprocessor and memory are supplied with a regulated voltage of about 2.1 volts from regulator 602, which is safely above the 2 volt level required. A portion of the analog circuitry is shown as a digital voltmeter, DVM. The battery is also connected through a current limiting circuit 605 to point 4, from which a capacitor 606 is connected to ground. Circuit 605 increases in effective resistance whenever the voltage at point 4 approaches a predetermined safety voltage greater than the 2.1 volt regulated voltage, e.g., 2.2 volts, as discussed in detail in connection with FIG. 6D. Circuit 605 may also be opened under control of the PPC chip to disconnect the output momentarily, such as when the microprocessor is turned on due to an output from gate 524. This provides further protection to the microprocessor since there is no loading from the output circuit at the moment when the microprocessor is turned on. An End of Life (EOL) circuit 682, referred to in connection with FIG. 6D, is used to sense whether the battery voltage has dropped to a predetermined value, suitably one between the safety voltage and the regulated voltage, e.g., 2.15 volts. A converter 607 may be used to raise the voltage level by a factor of 2 or greater, having an output connected through capacitor 608 to ground. Switch 609, controlled by the microprocessor, connects either point 4 or the output of converter 607 to provide power to the output circuit 610.

Figure 6B:
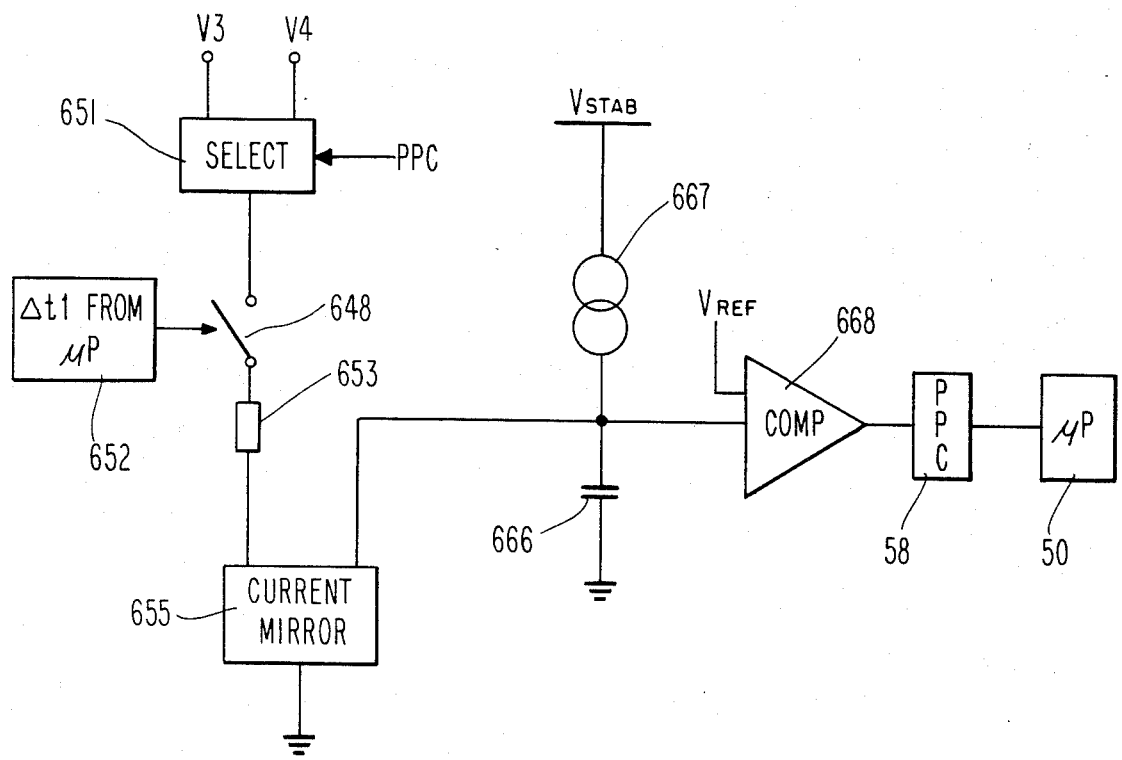
FIG. 6B is a simplified circuit diagram of the digital voltmeter used in the pacer of this invention.

Referring now to FIG. 6B, there is shown a simplified circuit diagram of the software-controlled digital voltmeter (d.v.m.) used in this invention. The voltage from either point 3 or 4 is gated at gate 651, under control of a control signal from controller 58. The selected voltage is connected through switch 648 which is closed for a time $\Delta t_1$, under microprocessor control as shown at block 652. High value resistor 653 together with the selected voltage constitutes a current source which is inputted to mirror circuit 655. The other current path into circuit 655 is connected from capacitor 666, which is also connected to current source 667 which delivers a relatively low current. The voltage on capacitor 666 is compared to a reference at 668, producing a signal which is connected to controller 58, which in turn can connect the derived data to microprocessor 50.

Figure 6C:
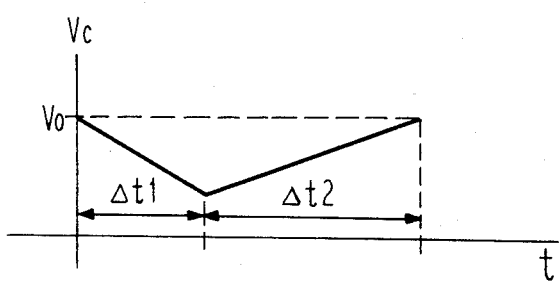
FIG. 6C is a timing diagram which illustrates the operation of the digital voltmeter.

The operation of the DVM is understood by reference to FIG. 6C along with FIG. 6B. The test starts with a capacitor voltage level of Vo. When switch 648 is closed, the controller timer is started and the current into circuit 655 discharges the capacitor, such the Vc decreases substantially linearly until the end of $\Delta t_1$. When switch 648 is opened after $\Delta t_1$, capacitor 666 recharges due to fixed current source 667. Since the discharge is proportional to the voltage being measured, so is the recharge time. When Vc comes back up to the reference level, comparator 668 produces a signal which stops the timer, giving a direct indication of the voltage.

Referring now to FIG. 6D, there is shown a circuit diagram for comparing the battery voltage $V_B$ to a predetermined reference $V_{ref}$, and controlling the current flow to the output as a function of such comparison. For the discussion on the circuit which flows, the following voltages are defined:

$V_B$: The output voltage from the pacer battery or power source. This voltage varies with time, due to energy depletion and build up of internal resistance in the battery.

$V_{off}$: Defined as an offset voltage, at which the pacer is programmed to begin to limit current to the output. For use with a lithium battery, and for purposes of illustration, $V_{off}=2.20$ volts.

$V_{EOL}$: Defined as the "End of Life" (EOL) voltage. At this voltage it is deemed that the pacer has reached the end of its useful life. Note that this does not mean that the pacer is no longer functioning, but it has reached a point where the battery voltage is sufficiently low that the pacer should be explanted. For purposes of illustration $V_{EOL}=2.15$ volts.

$V_{ref}$: Defined as reference voltage, relative to which the battery voltage is compared. In the preferred embodiment of this invention, $V_{ref}=2.10$, and is the stabilized voltage supplied for the pacer circuitry.

$V_{ref}$ is supplied from regulator circuit 602, or other separate refference circuit, and connected to the emitter of multiple collector transistor 670. The battery voltage $V_B$ is connected directly to the emitter of a second multiple collector transistor 671, and also to the input lead of switching device 680, the output of which is connected to the pacer output circuit. Battery voltage is also connected to EOL circuit 682, which is discussed below. Three of the collectors of transistor 670 are connected together to supply input current $I_{in}$ to a current mirror comprised of diode 677 and transistor 678. Two of the collectors of transistor 671 are connected to the output of transistor 678, providing the current mirror output current $I_{out}$. The same two collector terminals are connected to the gate terminal of switch device 680, to control the operating characteristics of that device. A higher voltage turns the switch on, and a lower voltage opens it (i.e., increases its impedance). The remaining collector terminal of transistor 670 is connected to a current source 675 which provides a constant current $I_K$. The base of transistor 670 is connected to source 675 through diode 672. The base of transistor 671 and its two remaining collector terminals are also connected through diode 673 to source 675.

In operation, the ratio of collector of transistors 670 and 671, which provide $I_{in}$ and $I_{out}$, determines the offset at which the circuit is balanced, and thus the voltage at the gate of device 680. Current generator 675 drives a constant current $I_K$, which is provided from a single collector of transistor 670 and from two collectors of transistor 671. $I_{in}$ of the current mirror is provided by the current from three collectors of the matched transistors 670, 671, while $I_{out}$ is normally provided by the current from just two collectors. As long as $V_B$ is well higher than $V_{ref}$, $I_{out}$ balances $I_{in}$ at a condition where the voltage connected to the gate of switch 680 is sufficiently high to make device 680 a substantial short circuit. The balance point is fine tuned by choosing diodes 672 and 673 such that $V_{be}$ for diode 673 is greater than $V_{be}$ for diode 672. However, under the circumstances where $V_B$ has dropped toward the predetermined $V_{off}$ (e.g. 2.20 volts), the amount of current contributed through diode 673 decreases, requiring an increase of current from transistor 670. Current generator 675 then pulls more current from transistor 670, causing an increase in $IJ_{in}$. Due to the action of the current mirror, transistor 678 is driven to a greater "on" condition, to the point where $I_{out}=I_{in}$. Thus, at the new balance point, the voltage drop across transistor 678 is decreased, dropping the control voltage connected to the gate of switch 680. When $V_B$ drops to $V_{off}$, switch 680 begins to limit the flow of current to the output. As $V_B$ drops even further, the switch becomes a higher resistance, thereby limiting current further, providing the desired current control when the battery voltage has dropped. Block 685 is shown as a switch having one output connected to ground and the other output connected to the gate of switch 680. When 685 is closed under a control signal from the PCC, switch 680 is caused to open entirely, thus preventing any current to the output, i.e., disabling the output circuit. This is done in particular situations, e.g. when voltage tests are performed or the microprocessor is turned on.

The EOL block 682 is any suitable circuit adjusted to reach an offset voltage at the desired EOL voltage, e.g. 2.15 volts.

Referring now to FIG. 7A, there is shown a flow diagram of the periodic program for determining end of life (EOL) by detecting when the battery terminal voltage, under normal load conditions, has dropped to a predetermined level. It is to be understood that EOL indicates a battery condition at which the pacer can continue operation, and does not indicate a literal end of functional operation. Rather, at the EOL signal, the pacing interval is increased to save energy and the condition may be monitored by external interrogation.

At the start of the test, a counter is examined to see if the test should be run. The counter may be set to any predetermined value, and is counted down each pacer cycle so that, for example, the EOL test may be done about once a week, once a day, or as frequently as desired. If the test is to be run, the time T at the start of the test is stored as $T_{start}$. Following this, point 3 is selected (see FIGS. 6A, 6B, 6C) and connected to the d.v.m., and switch 648 is closed for interval $\Delta t_1$. Also, the output is disabled under program control, by opening current limiter switch 605. Thus, the capacitor discharge illustrated in FIG. 6C is carried out under normal circuit load conditions, with the microprocessor running. When $\Delta t_1$ is timed out, the voltage point 3 is disconnected. The timer is then set to time out $\Delta t_2$, and the microprocessor is turned off for this interval. At timeout, $T_{stop}$ is stored, giving an indication of the battery voltage. The battery voltage is compared with an EOL reference, and the EOL flag is either set or reset. Following this, the output circuit is again enabled by closing switch 605. Thus, The EOL test is taken independent of the influence of the output circuit, but otherwise taking into account the loading of the analog and PPC circuits, as well as the microprocessor.

Referring now to FIG. 7B, there is shown a flow chart for an optional test of output voltage, taken at point 4 following a delivered pace pulse. This test incorporates the same d.v.m. steps, but is carried out only after making the pacer first run a complete fixed rate interval. The measurement flag is first checked to see if it has already been determined that the test is to be run. If the flag is not high, the program next checks to see if the counter is at zero, indicating that the test is to be done. For a "yes" response the measurement flag is set and the program determined whether the last cycle ended with a paced pulse or a sensed QRS. If the answer is "sense", the program skips and re-cycles until a cycle that has ended with a pace. Thereafter the measurement flag is reset, and a check is made to see if the EOL flag has been previously set. The sense circuit is then disabled, since it is a fixed interval cycle, and the microprocessor is stopped until time out. At time out the timer is reset, and the d.v.m. test is performed in the same manner as described in connection with the program of FIG. 7A. Following this, a stimulus is delivered, utilizing the microprocessor DMA mode, and the stimulus counter is incremented to update the count of delivered stimulus pulses, NS.

The output circuit is re-connected to the power supply at "enables recharge", and the measured voltage is compared to a predetermined reference to set the EOL flag or not. Since the test is conducted only after a full fixed rate pacing cycle, meaning that at least 2 consecutive stimulus pulses have been delivered, there is obtained a good indication of how low the voltage at point 4 drops under output load conditions.

Referring to FIG. 7C, there is illustrated a simplified diagram of a program for measuring load impedance. In the preferred embodiment this test is not run periodically, but may be initiated by an external request. The program waits for a stimulus, and then sets a fixed pacing interval. After time out of the next pacing interval, but just before delivery of a stimulus, the voltage at point 4 is first determined using the DVM subroutine. Then a stimulus is delivered and after disabling recharge of the output circuit and waiting a short delay to permit stabilization, the voltage is again measured. The first measured value, $V_1$, adjusted for the converter setting and for minor corrections, is the actual stimulating voltage; the difference between the two voltages, $V_2 - V_1$, represents the amount of charge delivered during a stimulus pulse. This information can be read out of the microprocessor, and used to determine also output current drain under a 100% pacing condition, and an indication of lead impedance.

We claim:

1. A pacer for use in a cardiac pacing system, having generating means for generating and delivering pacing pulses and sensing means for sensing natural heartbeat signals,
    pacing rate means for continuously determining the pacing rate of said pacer and the corresponding pacing interval, said pacing interval being the time from a prior delivered pacing pulse to a next succeeding pacing pulse,
    interval means for measuring the time interval elapsed from a prior pacing pulse or sensed heartbeat to a succeeding sensed heartbeat and determining means for determining whether said measured interval is less than said pacing interval by more than a predetermined factor, said pacing rate means having adjusting means for adjusting said pacing interval to vary as a function of said determination.

2. The pacer as described in claim 1, wherein said pacing rate means has first means for setting said pacing interval equal to said measured interval when said measured interval is not less than said pacing interval by more than said predetermined factor, and second means for decreasing said pacing interval only by said factor when said measured interval is less than said pacing interval by more than said factor.

3. The pacer as described in claim 2, wherein said second means comprises selection means for selecting the rate of decrease of said pacing interval.

4. The pacer as described in claim 1, wherein said pacer is a dual chamber type pacer having means for sensing beats in both the atrium and ventricle.

5. The pacer as described in claim 4, having means for pacing a patient's atrium and ventricle.

6. The pacer as described in claim 4, further comprising pvc sensing means for determining the presence of a premature ventricular contraction and said pacing rate means comprises increasing means for increasing said pacing rate as a function of said determination.

7. The pacer as described in claim 4, comprising enabling means for enabling operation of said adjusting means only in response to predetermined rate conditions.

8. The pacer is described in claim 1, comprising means for decreasing said pacing rate after each delivered pacing pulse, and means for limiting said pacing rate to a predetermined minimum value.

9. The pacer as described in claim 8, comprising means for limiting said pacing rate to a predetermind maximum value.

10. A cardiac pacer having pulse means for delivering pacing pulses to a patient's heart, the interval between successive ones of such pulses being a changeable pacing interval, including means for sensing the occurrence of natural heartbeats and means for determining whether a pulse or heartbeat has last occurred, further comprising means for determining each time interval from a second heartbeat to a next following second heartbeat or from a delivered pacing pulse to a next following sensed heartbeat, characterized by
    flywheel means for determining when said determined time interval does and does not decrease relative to the last prior interval by more than a first predetermined factor, and
    means for decreasing said pacing interval in accordance with a predetermined rate of change of rate upon determination of a relative interval decrease by more than said first factor; further characterized by overdrive means for reducing the escape interval and said pacing interval following a sensed heartbeat, and selection means for selecting operation of one of said flywheel means and said overdrive means following a sensed heartbeat.

11. The pacer as described in claim 10, in combination with means for delivering pacing pulses to a patient's ventricle.

12. The pacer as described in claim 10, in combination with means for delivering pacing pulses to a patient's atrium.

13. The pacer as described in claim 10, wherein said means for decreasing said pacing interval has means for selecting said predetermined function from a plurality of functions.

14. A method of operating a cardiac pacer, said pacer having a pacing pulse generator for generating and delivering pulses and having a changeable pacing interval, comprising the steps of
    generating and delivering pacing pulses,
    sensing the occurrence of natural heartbeats and delivered pacing pulses, and
    decreasing said pacing interval following a sensed heartbeat by only a first predetermined factor when the rate of occurrence of sensed heartbeats increases by more than a second predetermined factor.

15. The method of claim 14, wherein said sensing step comprises sensing ventricular heartbeats and said delivering step comprises delivering ventricular hearbeats.

16. The method of claim 14, comprising the steps of determining the time interval between successive heartbeats and setting said pacing interval equal to said determined interval when the increase in rate of occurrence of sensed heartbeats is less than said second predetermined factor.

17. A cardiac pacer having pulse means for delivering pacing pulses to a patient's heart, the interval between successive ones of such pulses being a changeable pacing interval, including means for sensing the occurrence of natural heartbeats and means for determining whether a pulse or heartbeat has last occurred, further comprising means for determining each time interval from a sensed heartbeat to a next following sensed heartbeat or from a delivered pacing pulse to a next following sensed heartbeat, characterized by flywheel means for determining when said determined time interval does and does not decrease relative to the last prior interval by more than a predetermined factor, said flywheel means including enabling means for enabling its operations, means for decreasing said pacing interval in accordance with a predetermined function upon determination of a relative interval decrease by more than said first factor, and means for programming when said flywheel enabling means is enabled.

* * * * *